United States Patent [19]

Ono et al.

[11] Patent Number: 5,169,635

[45] Date of Patent: Dec. 8, 1992

[54] PHOTORESPONSIVE LIPOSOME

[75] Inventors: Mitsunori Ono; Yoshihisa Tsukada, both of Kanagawa, Japan

[73] Assignee: Fuji Photo Film Co., Ltd., Kanagawa, Japan

[21] Appl. No.: 873,678

[22] Filed: Apr. 24, 1992

Related U.S. Application Data

[63] Continuation-in-part of Ser. No. 614,482, Nov. 16, 1990, abandoned.

[30] Foreign Application Priority Data

Nov. 17, 1989 [JP] Japan .................................. 1-299159

[51] Int. Cl.$^5$ ............................................. A61K 31/47
[52] U.S. Cl. ..................... 424/450; 264/4.1; 424/417; 424/420; 436/829; 428/402.2
[58] Field of Search ........................ 424/450, 420, 417; 428/402.2; 264/4.1, 4.3, 4.6; 260/403; 436/829

[56] References Cited

U.S. PATENT DOCUMENTS 4,193,983  3/1980  Ullman et al. ................. 424/450 X
4,625,014  11/1986  Senter ............................. 530/389.1
4,882,165  11/1989  Hunt et al. ......................... 424/450

OTHER PUBLICATIONS

Chem. Abs. 72:110546b (1970) Clark et al. Photoinitiated Hydrolysis of 3,5 Dimethoxybenzyl Dihydrogen Phosphates.

Primary Examiner—Thurman K. Page
Assistant Examiner—G. S. Kishore
Attorney, Agent, or Firm—Sughrue, Mion, Zinn, Macpeak & Seas

[57] ABSTRACT

A photoresponsive liposome which comprises a compound represented by the following general formula (I):

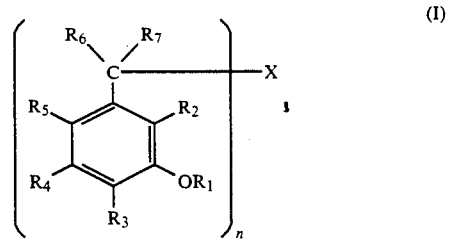

wherein $R_1$ is an alkyl group; $R_2$, $R_3$, $R_4$ and $R_5$, which may be the same or different, are selected from the group consisting of an alkyl group, a substituted alkyl group, an alkoxy group, a substituted alkoxy group, a halogen atom and a hydrogen atom; $R_6$ and $R_7$, which may be the same or different, are an alkyl group or a hydrogen atom; n is an integer of 1 to 2; and X represents a hydrophilic group, a hydrophobic group or a combination of hydrophilic and hydrophobic groups, bonded through a connecting group, provided that any of these hydrophilic and hydrophobic groups has such properties that the compound represented by the general formula (I) becomes available as a component forming the membrane of liposome.

6 Claims, 1 Drawing Sheet

PHOTORESPONSIVE LIPOSOME

This is a Continuation of Application No. 07/614,482 filed Nov. 16, 1990 now abandoned.

FIELD OF THE INVENTION

This invention relates to photoresponsive liposomes which are useful, especially, in the field of diagnostics, therapeutics, biochemistry and medical science. More particularly, this invention relates to a photoresponsive liposome prepared using a photoresponsive compound which contains a highly efficient photoreceptor group and is effective for controlling the amount of the content of liposomes released using light irradiation.

BACKGROUND OF THE INVENTION

Studies on artificial membranes and liposomes which respond to optical stimuli have been performed quite actively, in recent years. These studies have been directed in two main areas. That is, (1), embedding of photoresponsive groups into an oriented monomolecular film or dimeric film based, for example, on the reversible cistrans photoisomerization of azobenzenes (Chemistry Letters, p. 421, 1980) or on the conformational changes in photoresponsive proteins such as rhodopsin (J. Am. Chem. Soc., vol. 107, p. 7769, 1985) and (2) direct transfer of photoresponsive groups into liposome-forming lipids based, for example, on the covalent bonding of retinoic acid with a phospholipid (Photochemistry and Photobiology, vol. 37, p. 491, 1983) or on the covalent bonding of an o-nitrobenzyl group with a phospholipid (Chemistry Letters, p. 433, 1989).

Although each of these two areas has its own advantages and disadvantages, the second area where photoresponsive groups are transferred directly into a lipid material has that advantage that on/off release of the substance present can be distinguished more clearly than the situation in of the first area in which photoresponsive groups are embedded without covalent bonding.

An o-nitrobenzyl group is known as an effective photoresponsive group, but its reactivity is poor. Moreover, a fatal disadvantage has been pointed out in that this group is converted by cleavage into o-nitrobenzoaldehyde which is regarded as an extremely dangerous carcinogenic material. As a consequence, a highly efficient and safe photoreceptor group of the transfer type has been desired.

SUMMARY OF THE INVENTION

Therefore, an object of the present invention is to provide a photoresponsive liposome prepared using a photoresponsive compound which contains a highly efficient photoreceptor group and is effective for controlling using light irradiation the amount of the contents of a liposome.

Thus, the present invention provides a photoresponsive liposome which comprises a compound represented by the following general formula (I):

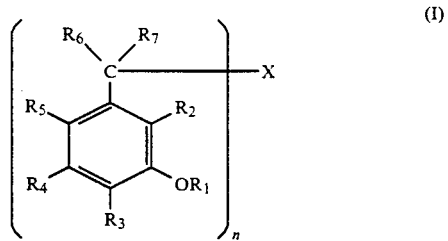

wherein $R_1$ is an alkyl group; $R_2$, $R_3$, $R_4$ and $R_5$, which may be the same or different, are selected from the group consisting of an alkyl group, a substituted alkyl group, an alkoxy group, a substituted alkoxy group, a halogen atom and a hydrogen atom; $R_6$ and $R_7$, which may be the same or different, are an alkyl group or a hydrogen atom; n is an integer of 1 to 2; and X represents a hydrophilic group, a hydrophobic group or a combination of hydrophilic and hydrophobic groups, bonded through a connecting group, provided that any of these hydrophilic and hydrophobic groups has such properties that the compound represented by the general formula (I) becomes available as a component forming the membrane of liposome (closed vesicles).

These and other objects and advantages of the present invention will be come apparent from the detailed description of this invention provided below.

BRIEF DESCRIPTION OF THE DRAWING

The Figure shows the effect of light irradiation on the periodic changes in the degree of release substance, carboxyfluorescein, from a liposome, wherein line 1 is the result obtained on continuous light irradiation for 80 minutes of liposomes obtained in Example 6, line 2 is a result obtained with intermittent light irradiation of intervals of 10 minutes-on and 10 minutes-off of liposomes obtained in Example 3, line 3 is the result obtained with intermittent light irradiation at intervals of 10 minutes-on and 10 minutes-off of liposomes obtained in Example 2, and line 4 is a result obtained in the dark.

DETAILED DESCRIPTION OF THE INVENTION

Figure 1:
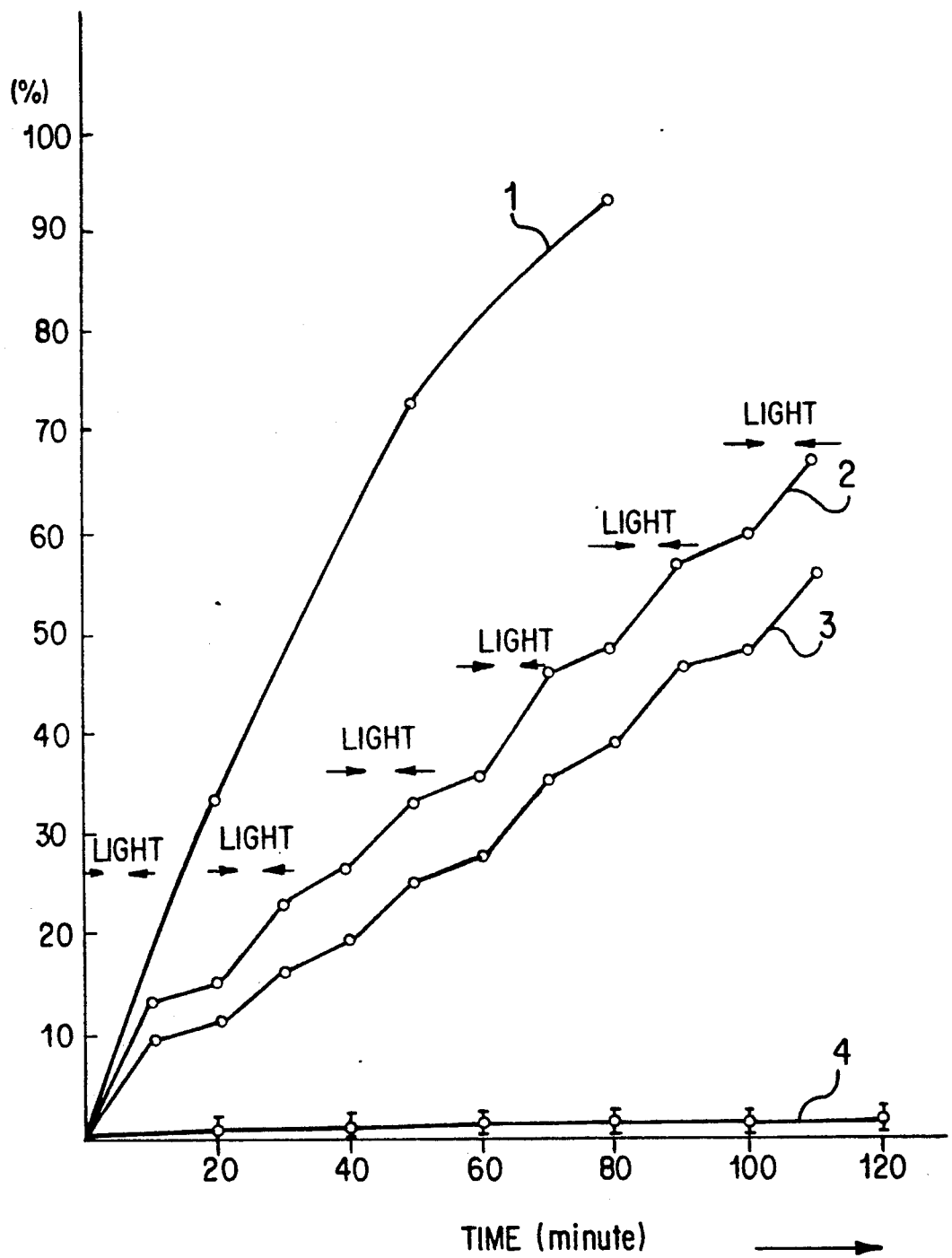

The objects of the present invention are accomplished by a photoresponsive liposome which comprises a compound represented by the following general formula (I) as the photoresponsive material:

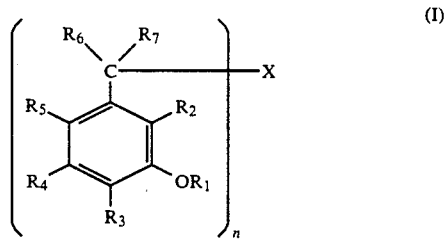

wherein $R_1$ is an alkyl group, preferably having 1 to 22 carbon atoms; $R_2$, $R_3$, $R_4$ and $R_5$, which may be the same or different, are selected from the group consisting of an alkyl group, a substituted alkyl group, an alkoxy group, a substituted alkoxy group, a halogen atom and a hydrogen atom; $R_6$ and $R_7$, which may be the same or different, are an alkyl group or a hydrogen atom; n is an integer of 1 to 2; and X represents a hydrophilic group, a hydrophobic group or a combination of hydrophilic and hydrophobic groups, bonded through a connecting group.

An alkyl group, an alkoxy group, a halogen atom, and a hydrogen are more preferred for $R_1$ to $R_5$.

More precisely, the alkyl group for $R_1$ to $R_5$ has preferably 1 to 22 carbon atoms, more preferably 1 to 18 carbon atoms. The substituted alkyl group for $R_1$ to $R_5$ has preferably 1 to 22 carbon atoms, more preferably 1 to 18 carbon atoms. Preferable substituent groups for the alkyl group are an aryl group, a halogen atom and the like. The alkoxy group for $R_1$ to $R_5$ has preferably 1 to 22 carbon atoms, more preferably 1 to 18 carbon atoms. The substituted alkoxy group for $R_1$ to $R_5$ has preferably 1 to 22 carbon atoms, more preferably 1 to 18 carbon atoms. Preferable substituent groups for the alkoxy group are an alkyl group having 1 to 3 carbon atoms, an aryl group, a halogen atom and the like. The halogen atom includes chlorine, bromine, fluorine and iodine, with chlorine being most preferred. For $R_6$ and $R_7$, a methyl group and a hydrogen atom are preferable as the alkyl group, but a hydrogen atom is most preferable as $R_6$ and $R_7$.

X in the formula (I) can be any hydrophilic and hydrophobic group which have properties such that the compound represented by the general formula (I) becomes available as a component forming a liposome membrane (closed vesicles). Preferred hydrophobic residues are alkyl groups having 7 to 21 carbon atoms. Preferred hydrophilic residues include cations, anions, betaine structures and hydroxyl groups. Suitable and preferred connecting groups for X can be ether groups, ester groups (phosphoric esters and sulfonic esters), urethane bonds and carbonic ester bonds are preferable.

In general, the balance of hydrophilic and hydrophobic groups in a lipid molecule determines the type of molecular assembly in water. The HLB (hydrophiliclipophilic balance) is generally used as a marker to identify the balance of hydrophilic and hydrophobic groups in such amphipatic substances. In principle, a higher HLB value indicates a stronger hydrophilic nature. Since the membrane of liposomes takes the form of lamella as the basic structure, a material having conveniently balanced hydrophilic and hydrophobic groups can be used to form stable liposomes.

The HLB value can be calculated using the following formula.

$$HLB = 11.7 \log \frac{Mw}{Mo} + 7$$

wherein Mo represents molecular weight of an alkyl group present in the compound and Mw is obtained by subtracting Mo from the overall molecular weight of the compound.

It is possible to determine the balance of the hydrophilic and hydrophobic groups in the compound represented by the general formula (I) in the present invention on the basis of the HLB value, and preferable HLB value is in the range of from 2 to 18. The HLB is described in detail in Kagaku-no Ryoiki, vol. 7, pp. 689 to 698, 1953.

Compounds having the following formulae are most preferred as compounds of the general formula (I).

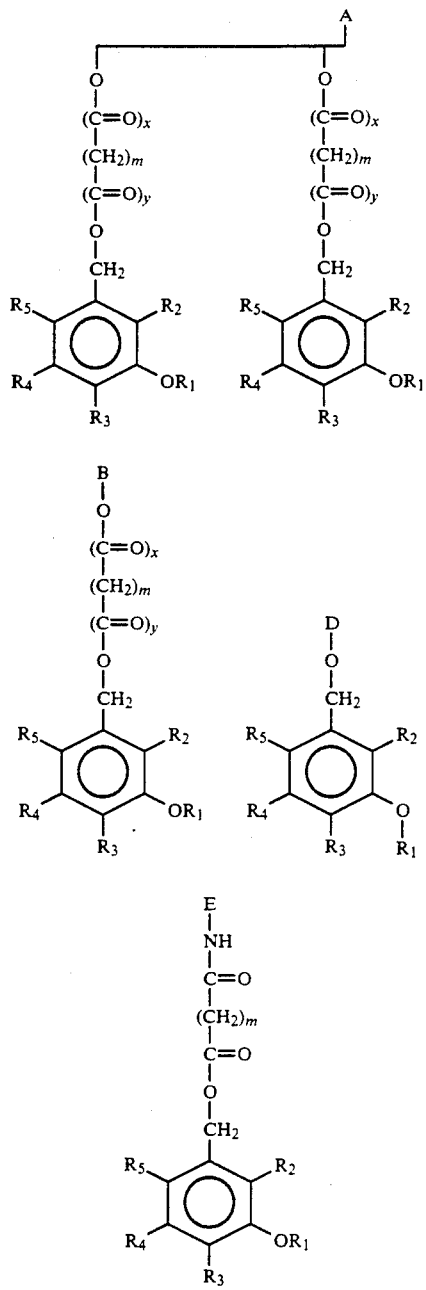

wherein $R_1$ to $R_5$ are the same as discussed for the general formula (I), m is an integer of 6 to 20, x and y represent 0 to 1 (where X and Y are not simultaneously 0), where A represents any of the following groups,

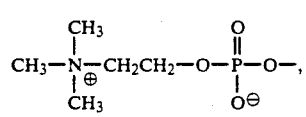

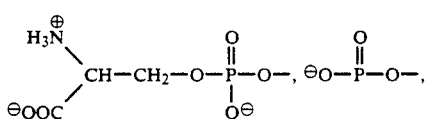

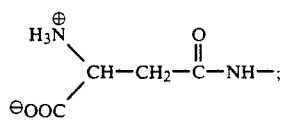
B represents any of the following groups,
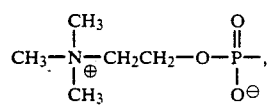
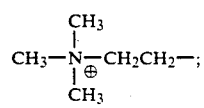
D represents any of the following groups, and
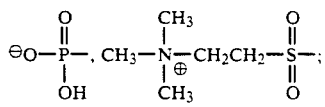
E represent any of the following groups
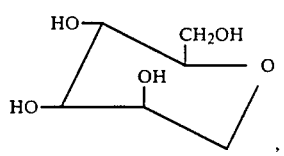
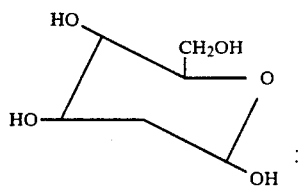
Example of compounds represented by the general formula (I) are given below by way of illustration and not by way of limitation.
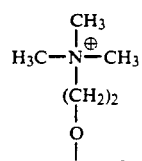
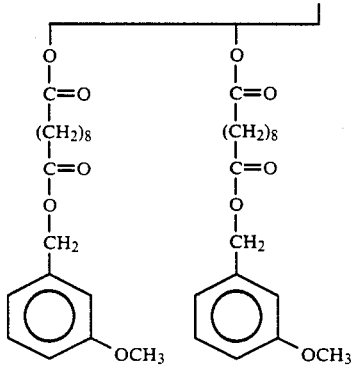
I-1
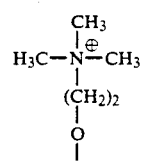
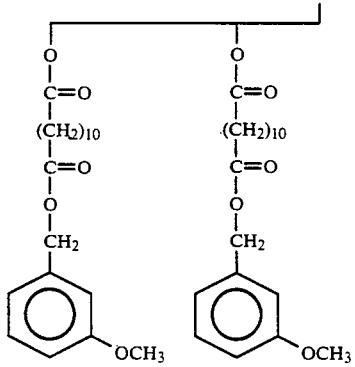
I-2

-continued
I-3
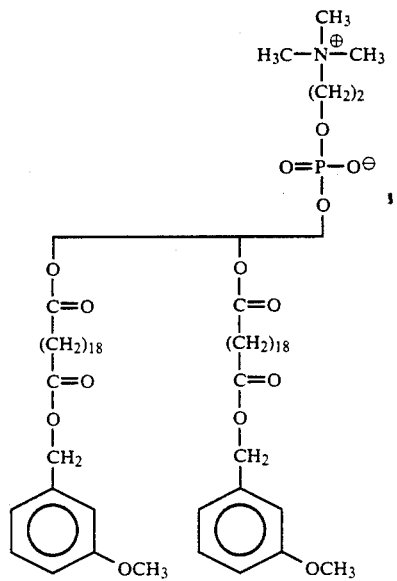
I-5
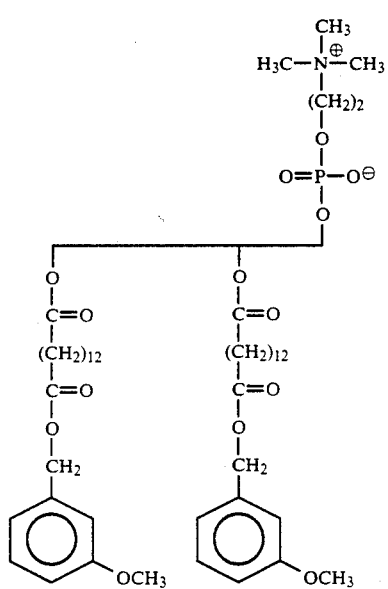
I-4
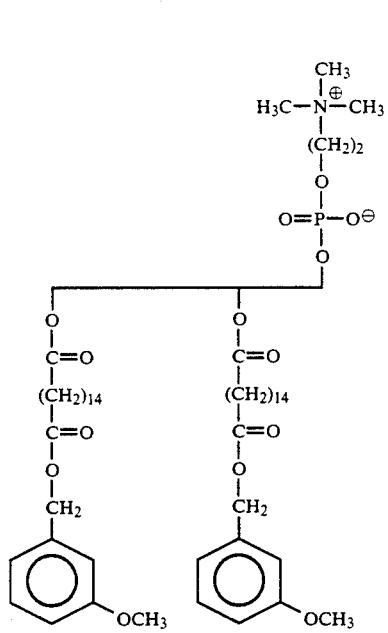
I-6
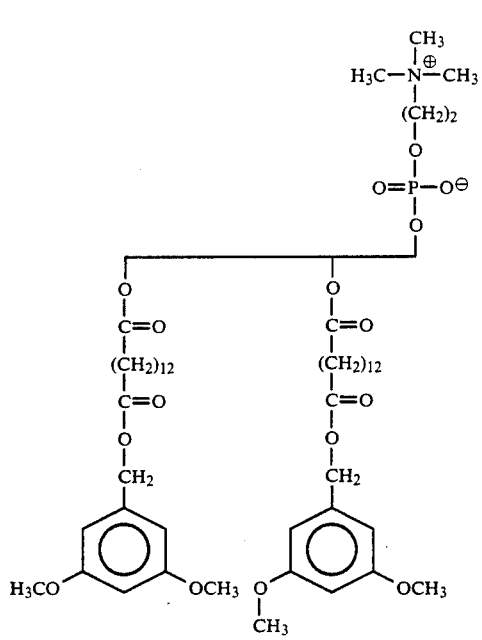

-continued
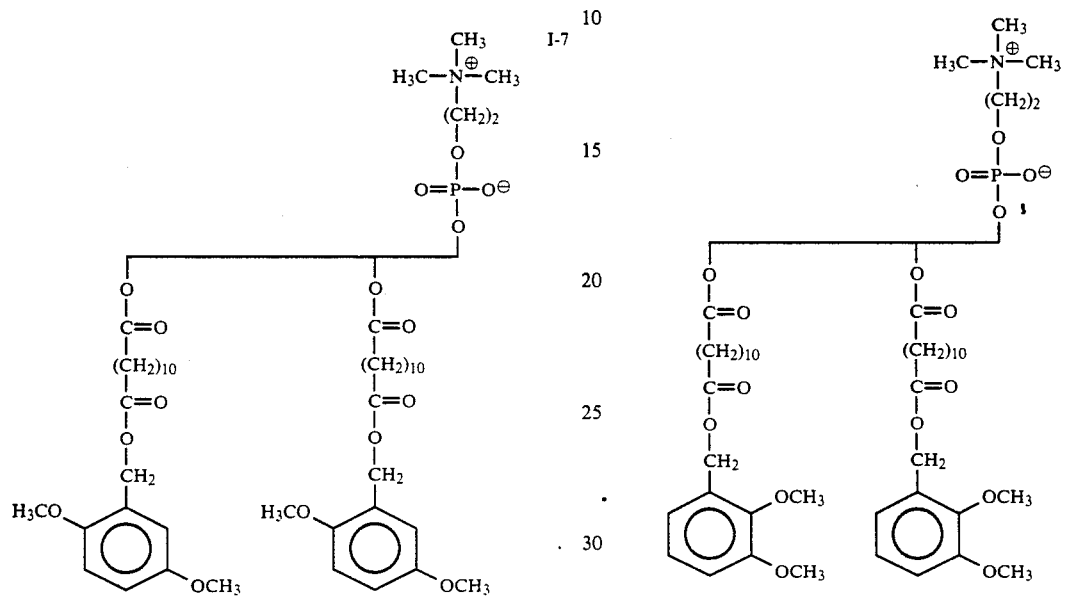
-continued
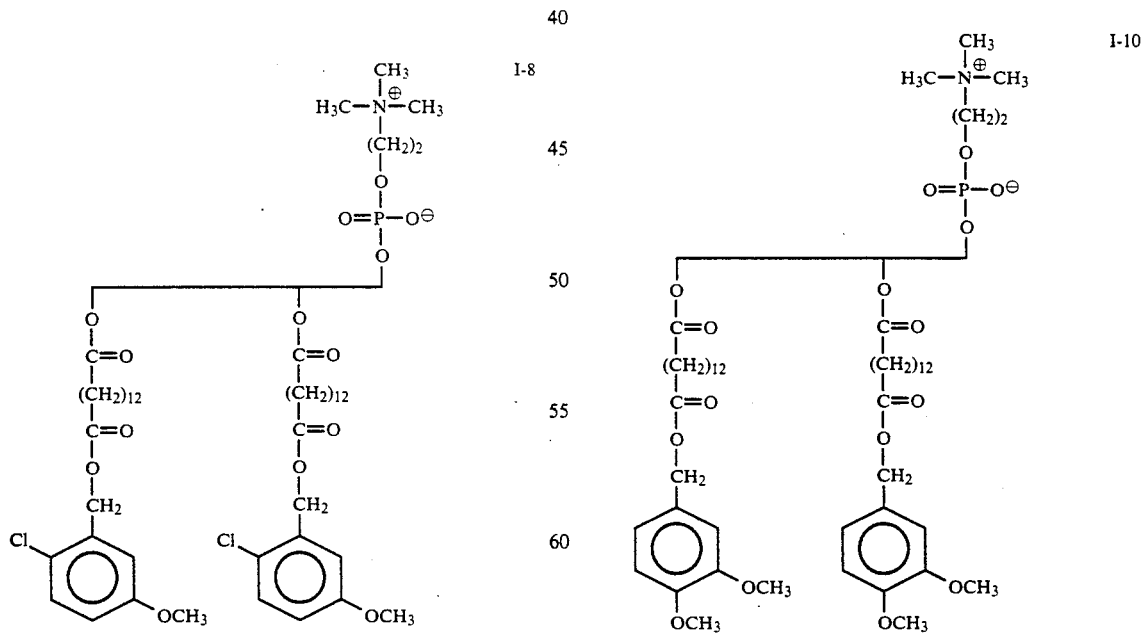

-continued
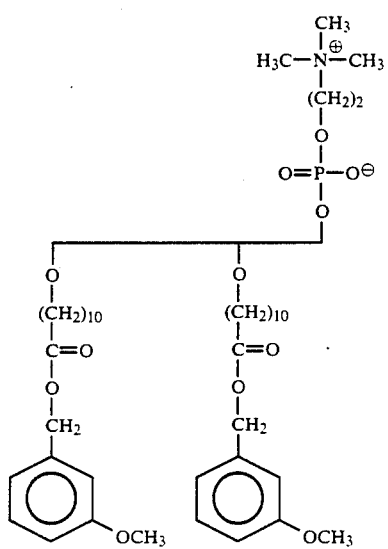
I-11
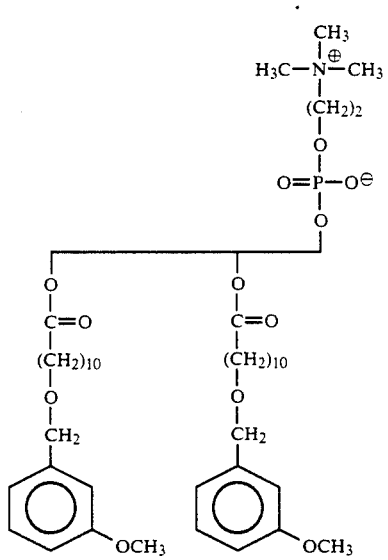
I-12
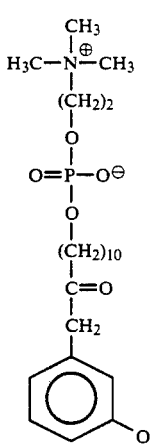
I-13
-continued
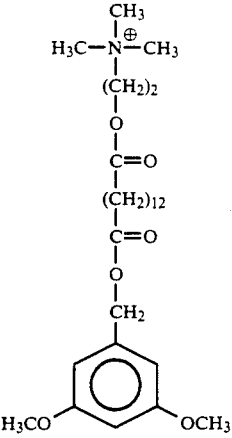
I-14
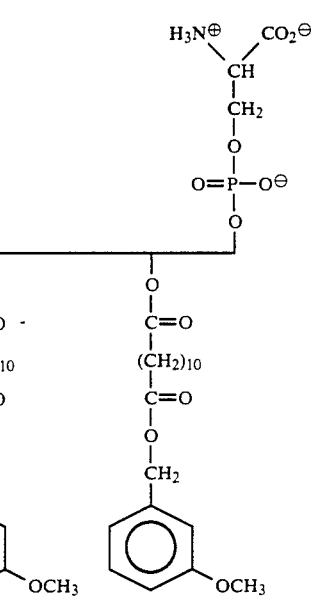
I-15
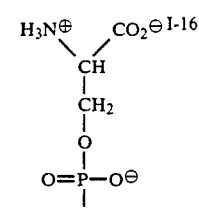
I-16

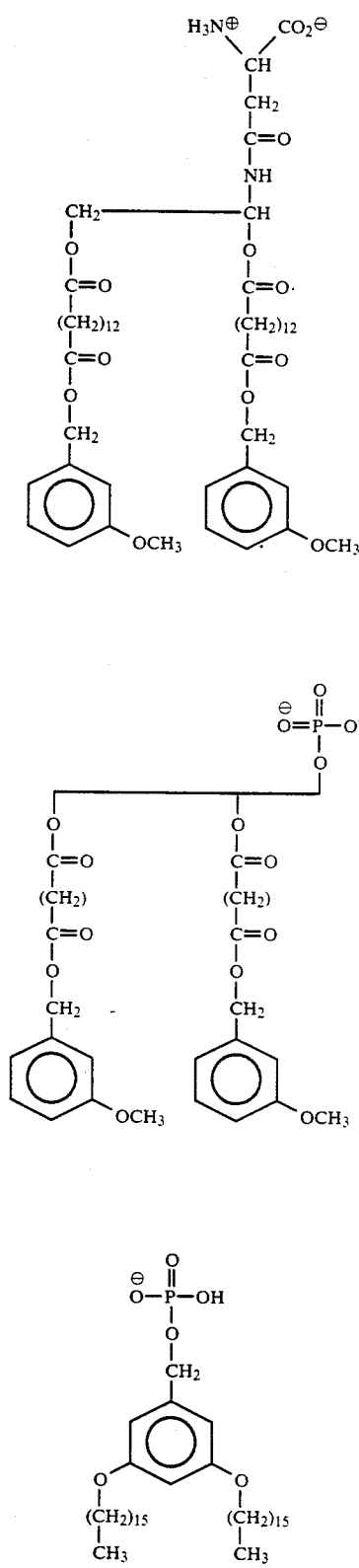
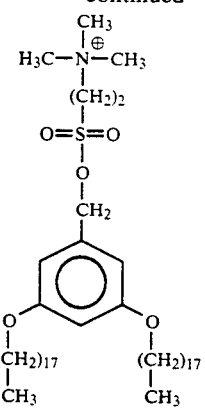
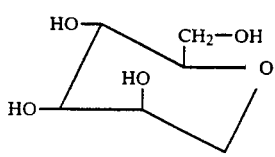
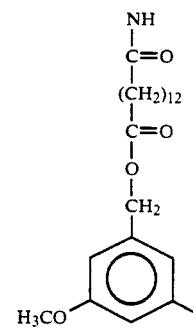
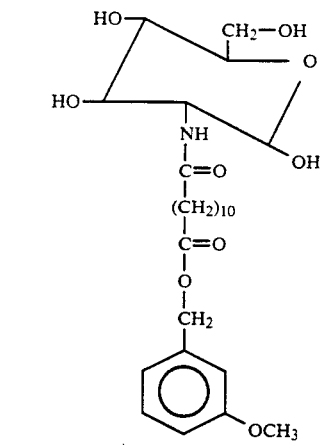
Compounds I-1, I-2, I-3, I-5, I-6, I-7, I-8, I-9, and I-10 are preferred among them.
The compound used in the present invention can be synthesized by using of various prior art techniques. Some examples of the synthesis of the compound used in the present invention are given below.

Outline of Synthetic Pathway

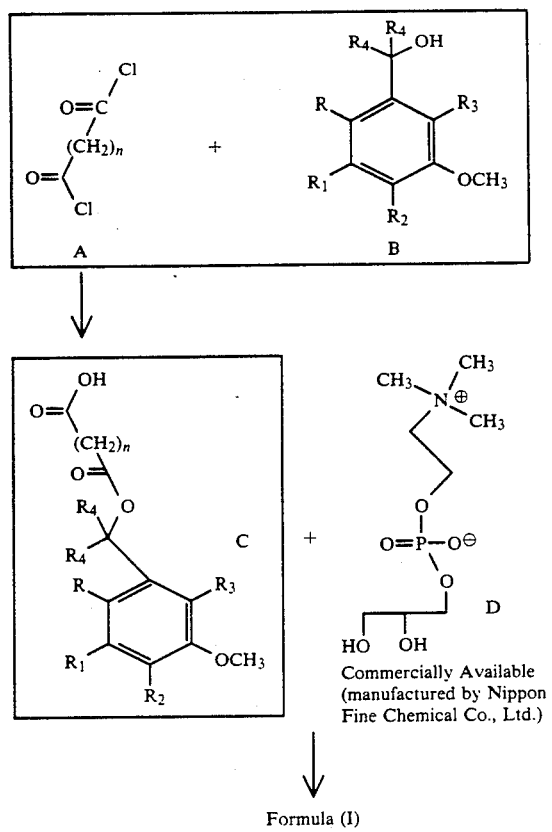

Formula (I)
Compound used in the present invention

Synthesis of Compound I-1 (1) Synthesis of compound A (n=8)

100 g of 1,8- octane dicarboxylic acid was mixed with 100 ml of thionyl chloride and 100 ml of toluene and the mixture was subjected to reflux with heating for 10 hours. After confirming the disappearance of the absorbance of a carboxylic acid and appearance of the absorbance of an acid chloride group using IR analysis, the resulting reaction solution was concentrated under a reduced pressure to obtain quantitatively 118 g of the compound A (n=8).

The physical properties of the compound A are as follows.

IR (-COCl), 1800 cm$^{-1}$

(2) Synthesis of Compound C (n=8; R$_1$ to R$_4$=H)

300 ml of a tetrahydrofuran (THF) solution containing 13.8 g of m-methoxybenzyl alcohol and 10.1 g of triethylamine was added dropwise with stirring to 200 ml of a THF solution containing 23.9 g of Compound A (n =8) and the stirring was continued for 5 hours at room temperature. The resulting reaction solution was mixed with 200 ml of saturated sodium hydrogen carbonate solution, stirred for 20 minutes and then extracted with 500 ml of ethyl acetate. The resulting water layer was again extracted with 500 ml of ethyl acetate and the organic layer was collected and dried using sodium sulfate. After removing the sodium sulfate by filtration, the filtered solution was concentrated under reduced pressure to obtain a brown oily mixture. Thereafter, the thus obtained reaction mixture was subjected to silica gel column chromatography (elution system; hexane/ethyl acetate 3/1 on a volume/volume basis) to obtain 15 g of purified oily Compound C (n=8) in a yield of 46%.

The physical properties of the thus purified Compound C were as follows.

IR (neat); $\vee$ (ester) 1740 cm$^{-1}$, $\vee$ (carboxylic acid) 1700 cm$^{-1}$

(3) Condensation Reaction 60 ml of a methanol solution of Compound D (20% on w/v basis, commeacially available from Nippon Fine Chemical Co., Ltd.) was concentrated under a reduced pressure and then mixed with 700 ml of ethanol. In 240 ml of 95% ethanol was dissolved 20 g of cadmium chloride (CdCl$_2$.2.5.H$_2$O) and the solution was added dropwise to the ethanol solution of Compound D. After standing at 4° C. for 12 hours, the resulting white precipitate was collected by filtration and washed twice with ethanol and then twice with diluted ether. By drying the washed precipitates, 22.0 g of white powder of (Compound D)$_2$.(CdCl$_2$)$_3$ was obtained.

4.6 g of the thus prepared CdCl$_2$ salt of Compound D was added to 100 ml of a chloroform solution of 12.9 g of Compound C (n=8), 2.4 g of 4-dimethylaminopyridine and 8.3 g of dicyclohexylcarbodiimide and the mixture was stirred at room temperature for 3 days. The resulting reaction mixture was purified by subjecting it to an ion-exchange chromatography using Amberlite IR-120B (elution system, chloroform/methanol/water=4/5/1) and then to silica gel chromatography (elution system, chloroform/methanol/water=65/25/4). The eluent thus obtained was concentrated under reduced pressure, mixed with 100 ml of chloroform and then washed with water. Thereafter, the washed solution was dried using sodium sulfate and concentrated under a reduced pressure to obtain 5.0 g of the Compound I-1 in an oily form in a yield of 70%.

The physical properties of the thus obtained Compound I-1 were as follows.

IR (neat); $\vee$ (ester)=1740 cm $^{-1}$ $^1$H NMR (CDCl$_3$); $\delta$=1.30 (br s, 16H, CH$_2$), 1.64 (m.8H, CH$_2$CH$_2$CO), 2.37 (m.8H, CH$_2$CO), 3.41 (br s, 9H, N(CH$_3$)$_3$), 3.81 (s, 6H, OCH$_3$), 3.88 to 4.45 (m.8H, CH$_2$O and CH$_2$N), 5.05 (s.4H, CH$_2\phi$), 5.19 (m.1H, CHO) and 6.85 to 7.34 (m.8H, $\phi$).

FAB-MS; 866 (M+H)$^+$

Synthesis of Compound I-3 (R$_1$ to R$_4$=H)

Compound I-3 was prepared using the same procedures as described above for the synthesis of Compound I-1 except that the starting material was changed. The physical properties of Compound I-3 produced were as follows.

IR (KBr); $\vee$ (ester)=1740 cm$^{-1}$ $^1$H NMR (CDCl$_3$); $\delta$=1.38 (br s, 32H, CH$_2$), 1.65 (m.8H, CH$_2$CH$_2$CO), 2.36 (m.8H, CH$_2$CO), 3.38 (s.9H, N(CH$_3$)$_3$), 3.80 (s.6H, OCH$_3$), 3.89 to 4.42 (m.8H, CH$_2$O and CH$_2$N), 5.01 (s.4H, CH$_2\phi$), 5.18 (m.1H, CHO) and 6.85 to 7.34 (m.8H, $\phi$).

FAB-MS; 987 (M+H)$^+$

Synthesis Compound I-4 (R$_1$ to R$_4$=H)

Compound I-4 was prepared using the same procedures as described for the synthesis of Compound I-1 except that the starting material was changed. The physical properties of Compound I-4 were as follows.

IR (KBr); $\vee$ (ester)=1740 cm$^{-1}$ $^1$H NMR (CDCl$_3$); δ=1.38 (br s, 32H, CH$_2$), 1.65 (m.8H, CH$_2$CH$_2$CO), 2.36 (m.8H, CH$_2$CO), 3.38 (s.9H, N(CH$_3$)$_3$), 3.80 (s.6H, OCH$_3$), 3.89 to 4.42 (m.8H, CH$_2$O and CH$_2$N), 5.01 (s.4H, CH$_2$φ), 5.18 (m.1H, CHO) and 6.85 to 7.34 (m.8H, φ).

FAB-MS; 987 (M+H)+

Compounds I-2, I-5, I-6, I-7, I-8, I-9 and I-10 can also be synthesized easily in the same manner as described above.

Any well-known prior art technique, as well as a stable plerilamellar vesicle method (SPLV method) as described in S. M. Gruner et al. in Biochemistry (vol. 24, p. 2833, 1985), is useful for the production (preparation) of functional liposomes of the present invention. Examples of suitable prior art techniques which can be used for the production (preparation) of liposomes include a vortexing method, an ultrasonic treatment method, a surface active agent treatment method, a reverse phase evaporation method (REV method), an ethanol injection method, an ether injection method, a pre-vesicle method, a French press extrusion method, a Ca$^{2+}$ fusion method, an annealing method, a freezing-thawing fusion method and a W/O/W emulsion method. In other words, the photoresponsive liposome of the present invention can be prepared using any of these prior art techniques or any other liposome-preparation method, except that the formation of liposomes is performed in the presence of the compound as represented by the general formula (I).

The main materials comprising the liposome of the present invention can be any of the materials conventionally used in the prior art liposome preparation techniques. Examples of these materials include natural lecithins (yolk lecithin and soy bean lecithin, for example), a phospholipid selected from the group consisting of dipalmitoylphosphatidylcholine (DPPC), dimyristoylphosphatidylcholine (DMPC), distearoylphosphatidylcholine (DSPC), dioleoylphosphatidylcholine (DOPC), dimyristoylphosphatidylethanolamine (DMPE), dipalmitoylphosphatidylglycerol (DPPG), dimyristoylphosphatidic acid (DMPA) and the like. A mixture of two or more of these phospholipids, and a mixture of any of these materials and cholesterols can be used, if desired.

The photoresponsive compound of the present invention may be used alone or as a mixture with any of the above-described prior art liposome forming materials.

With regard to the material to be incorporated into liposomes, there are no special limitations in terms of its hydrophilic property, water solubility and the like. The following materials are given as examples by way of illustration and not by way of limitation: carcinostatic agents such as adriamycin, actinomycin, mitomycin, 1-β-arabinofuranosyl cytosine, bleomycin and cisplatin; antiviral agents such as interferon; antibiotic agents such as aminoglycosides (gentamycin for example) and β-lactams (sulbenicillin, cefotium and cefmenoxime); peptide hormone preparations such as TRH ryuburolite and insulin; enzyme preparations such as lysozyme, asparaginase and glycosidases; immunopotentiators such as muramyl dipeptide and muramyl tripeptide; and proteins such as immunoglobulins and various toxins.

The effect of the present invention is described below.

The photoresponsive compound of the present invention is effective for controlling the amount of the material incorporated into the liposome released as a result of light irradiation. This effect is achieved using the photoresponsive compound represented by the general formula (I) alone or as a mixture with any of the commonly used liposome forming materials. The photoresponsive group in the compound of the present invention is an m-alkoxybenzyl moiety in which cleavage of its bonding occurs when it absorbs light at 200 to 300 nm. The following shows an example of the bond cleavage system of an m-alkoxybenzyl group in a photoresponsive compound wherein R$_1$ is CH$_3$ and each of R$_2$ to R$_6$ is H.

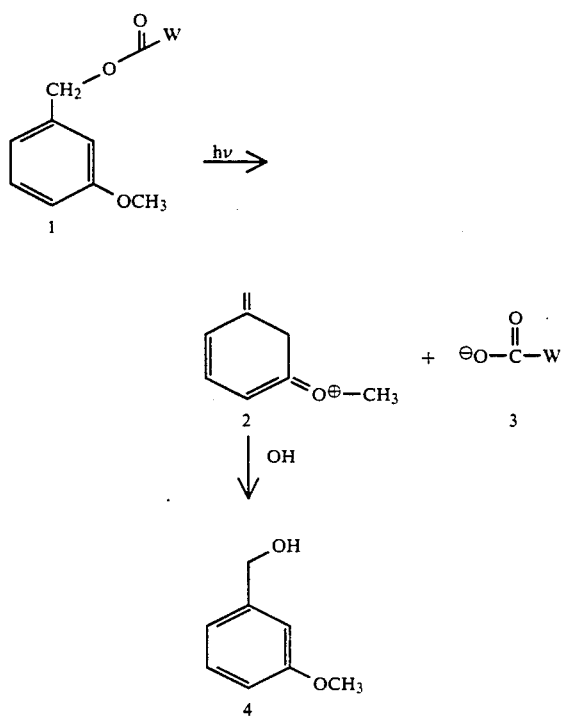

Because of the unstable nature of intermediate 2, is converted into benzyl alcohol 4 by action with water used as the solvent. One of the advantages of this photoresponsive compound is its lower toxicity than that of the o-nitrosobenzaldehyde. The compound 1 having well-balanced hydrophilic and hydrophobic properties is useful as the main component of liposomes, but the balance is broken as the result of irradiation with light. Subsequent cleavage of the bonding and formation of a water soluble group (carboxylate 3 for example), causes a disorder, a defect and the like in the liposome membrane.

The effect of the photoresponsive group of the present invention is also evident from the following model experiments in a solution system.

Evaluation of the Effect of Substituent Groups in a Solution System

Compounds Used:

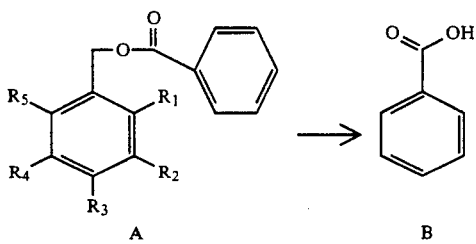

Light Source: 5W low pressure mercury lamp (254 nm)
Quartz cell; 2 mM substrate acetonitrile/phosphate buffer pH=7.0
Room temperature

| | | | Relative Photo Reaction Efficiency* | | | |
|---|---|---|---|---|---|---|
| No. | $R_1$ | $R_2$ | $R_3$ | $R_4$ | $R_5$ | Cleavage (A) $\min^{-1} \times 10^{-2}$ | Formation (B) $\min^{-1} \times 10^{-2}$ |
| 1 | $OCH_3$ | $OCH_3$ | H | H | H | 7.1 | 6.6 |
| 2 | H | $OCH_3$ | $OCH_3$ | H | H | 14.5 | 12.6 |
| 3 | H | $OCH_3$ | H | $OCH_3$ | H | 103 | 69.2 |
| 4 | H | $OCH_3$ | H | H | $OCH_3$ | 37.6 | 35.5 |
| 5 | H | $OCH_3$ | Cl | H | H | 8.1 | 6.0 |
| 6 | H | $OCH_3$ | H | H | Cl | 17.4 | 10.1 |
| 7 | H | $OCH_3$ | H | H | H | 46.5 | 47.7 |
| 8 | $NO_2$ | H | H | H | H | 4.1 | 3.0 |

* Rate constant $\times \dfrac{1}{1 - 10^{-O.D.}}$ (O.D. represents absorbance at 254 nm)

As is evident from a comparison of the results shown in the above table, the photoresponsive group of the present invention is superior to the commonly used photoreceptor group ($-NO_2$, No. 8 in the table) in terms of both cleavage of the substrate (A) and formation of the hydrophilic group (B).

These results show the marked effect of the present invention.

The following Examples of the present invention are given below by way of illustration and not by way of limitation.

EXAMPLE 1

A thin film of Compound I-1 was prepared by dissolving 30 mg of Compound I-1 in 10 ml of chloroform and then distilling off the solvent under reduced pressure. After drying thoroughly, the thus prepared thin film was subjected to vortexing for 15 minutes in the presence of 3 ml of a phosphate buffer (pH 7.0) containing 200 mM NaCl.

Destruction of the thus prepared liposomes was observed microscopically when they were exposed to light from a 250 W of xenon lamp.

EXAMPLE 2

A mixture of 27 mg of dipalmitoylphosphatidylcholin (m.W, 735) and 4 mg of Compound I-3 (m.W, 978) was dissolved in 10 ml of chloroform and then the solvent was distilled off under reduced pressure at 50° C. on a hot water bath. After drying thoroughly, the thus prepared thin film was subjected to vortexing for 15 minutes at 70° C. in the presence of 3 ml of a buffer solution of carboxyfluorescein (150 mM; Tris-HCl buffer, pH 7.0; no NaCl) and then treated for 5 minutes with a probe type sonicator.

Thereafter, the sonicated sample was subjected to gel filtration using Sepharose 4B, and each of the resulting fractions was checked for mean particle size and phospholipid concentration of the thus obtained liposomes in order to obtain a sample for Example 8.

EXAMPLE 3

The preparation of liposomes was performed by repeating the process of Example 2, except that 27 mg of dipalmitoylphosphatidylcholin (m.W, 735) and 15 mg of the Compound I-3 (m.W, 938) were used.

EXAMPLE 4

The preparation of liposomes was performed by repeating the process of Example 2, except that 27 mg of dipalmitoylphosphatidylcholin (m.W, 735) and 4 mg of the Compound I-4 (m.W, 966) were used.

EXAMPLE 5

The preparation of liposomes was performed by repeating the process of Example 2, except that 27 mg of dipalmitoylphosphatidylcholin (m.W, 735) and 15 mg of the Compound I-4 (m.W, 966) were used.

EXAMPLE 6

The preparation of liposomes was performed by repeating the process of Example 2, except that 27 mg of dipalmitoylphosphatidylcholin (m.W, 735) and 4 mg of the Compound I-6 (m.W, 967) were used.

EXAMPLE 7

The preparation of liposomes was performed by repeating the process of Example 2, except that 27 mg of dipalmitoylphosphatidylcholin (m.W, 735) and 15 mg of the Compound I-6 (m.W, 967) were used.

EXAMPLE 8

A fraction containing liposomes with mean particle size of 250 to 300 nm was selected from each of the thus prepared liposome samples produced in Examples 2 to 7 described above, and the phospholipid concentration of the thus selected samples was adjusted to 1 mM.

Each of the adjusted samples was then transferred into a quartz cell and exposed to light from a 6 W low pressure mercury lamp at a distance of 5 cm from the light source and at 25° C. and pH 7.0, in order to trace the leakage of carboxyfluorescein from inside the liposomes using a fluorescence measurement. As a result, leakage of carboxyfluorescein caused by the irradiation of light was observed in every liposome checked.

The results obtained using liposomes of Examples 2, 3 and 6 in these leakage experiments are shown in the Figure. The liposomes of Examples 2 and 3 were exposed to light at an intermittent light irradiation of intervals of 10 minutes-on and 10 minutes-off, while those of Example 6 were exposed to light continuously for 80 minutes.

In the Figure, the ordinate indicates the percentage of carboxyfluorescein leaked and the abscissa indicates time. These results show that almost 100% of carboxyfluorescein contained in the liposomes leaked out after 80 minutes of continuous exposure to light in comparison with the leakage from liposomes of Examples 2, 3 and 6 under dark conditions.

In the case of the intermittent exposure to light at 10 minute intervals, a significant difference in the leakage was observed between the light and dark conditions, indicating the presence of an on/off function although exact correspondence was not achieved.

Similar tendencies were observed when the kind and amount of the compound of the present invention were changed.

Thus, it is apparent that the present invention provides a photoresponsive liposome prepared using a photoresponsive compound which contains a highly efficient photoreceptor group and is effective for controlling the amount of the contents of the liposomes released using light irradiation.

While the invention has been described in detail and with reference to specific embodiments thereof, it will be apparent to one skilled in the art that various changes and modifications can be made therein without departing from the spirit and scope thereof.

What is claimed is:

1. A photoresponsive liposome that lyres on exposure to light which comprises a photocleavable compound represented by the following general formula (I):

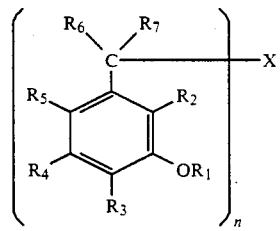

wherein $R_1$ is an alkyl group; $R_2$, $R_3$, $R_4$ and $R_5$, which may be the same or different, are selected from the group consisting of an alkyl group, a substituted alkyl group, an alkoxy group, a substituted alkoxy group, a halogen atom and hydrogen atom; $R_6$ and $R_7$, which may be the same or different, are an alkyl group or a hydrogen atom; n is an integer of 1 to 2; and X represent a hydrophilic group, a hydrophobic group or a combination of hydrophilic and hydrophobic groups, bonded through a connecting group, provided that any of these hydrophilic and hydrophobic groups has such properties that the compound represented by the general formula (I) becomes available as a component forming the membrane of liposome, wherein X is

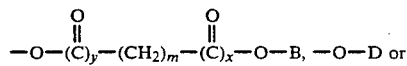

-continued

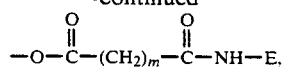

and wherein A is

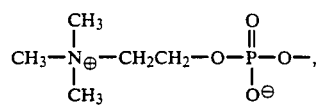

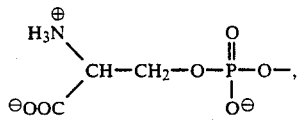

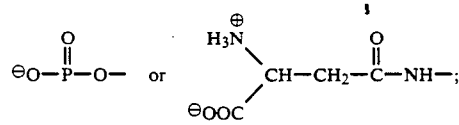

B is 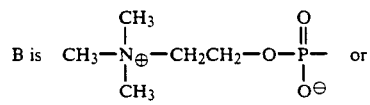

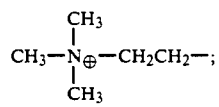

D is 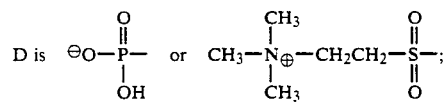

E is 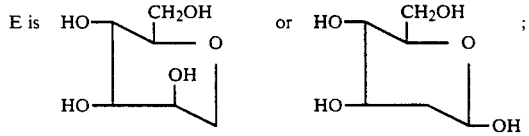

x and y each is 0 or 1 and m is an integer of 6 to 20.

2. The photoresponsive liposome of claim 1, wherein $R_1$ is alkyl group having 1 to 22 carbon atoms.

3. The photoresponsive liposome of claim 1, wherein $R_2$, $R_3$, $R_4$ and $R_5$ are selected from the group consisting of an unsubstituted or substituted alkyl group having 1 to 22 carbon atoms, an unsubstituted or substituted alkoxy group having 1 to 22 carbon atoms, a halogen atom or a hydrogen atom.

4. The photoresponsive liposome of claim 1, wherein at least one of $R_6$ and $R_7$ is a hydrogen atom.

5. The photoresponsive liposome of claim 1, wherein the compound of the formula (I) has a hydrophilic/lipophilic balance ranging from 2 to 18.

6. The photoresponsive liposome of claim 1, wherein the liposome contains therein at least one agent selected from the group consisting of a carcinostatic agent, an anti-viral agent, an antibiotic agent, a peptide hormone, an enzyme, an immunopotentiator, a immunoglobulin and a toxin.

* * * * *